US00PP17116P3

(12) United States Plant Patent
Drewlow

(10) Patent No.: US PP17,116 P3
(45) Date of Patent: Sep. 26, 2006

(54) ***KALANCHOE* PLANT NAMED 'FOREVER MIDI PINK MORNING'**

(50) Latin Name: *Kalanchoe blossfeldiana*
Varietal Denomination: Forever Midi Pink Morning

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/209,363

(22) Filed: Aug. 23, 2005

(65) Prior Publication Data

US 2006/0041970 P1 Feb. 23, 2006

Related U.S. Application Data

(60) Provisional application No. 60/603,845, filed on Aug. 23, 2004.

(51) Int. Cl.
*A01H 5/00* (2006.01)

(52) U.S. Cl. ..... Plt./335

(58) Field of Classification Search ..... Plt./335, Plt./339, 338
See application file for complete search history.

*Primary Examiner*—Kent Bell
*Assistant Examiner*—June Hwu

(74) *Attorney, Agent, or Firm*—The Webb Law Firm

(57) ABSTRACT

A new and distinct cultivar of *Kalanchoe* plant named 'Forever Midi Pink Morning', characterized by mounded to semi-upright, dense and uniform plant habit; freely branching growth habit; numerous light yellow, pinkish-white, and pink colored flowers; and excellent post-production longevity.

1 Drawing Sheet

Botanical classification: *Kalanchoe blossfeldiana.*
Varietal denomination: 'Forever Midi Pink Morning'.

BACKGROUND OF INVENTION

The present invention comprises a new and distinct cultivar of *Kalanchoe blossfeldiana*, known by the varietal name 'Forever Midi Pink Morning'. The new variety is a product of a planned breeding program conducted in Lompoc, Calif. The purpose of the breeding program was to create new cultivars with unique flower colors, fuller flower clusters over the top of the plants, compact growth habits, and free-branching habits. The new variety was selected from a seedling population, which originated from a cross-pollination of a proprietary selection of *Kalanchoe blossfeldiana* identified as code number 95-464-2, not patented, as the female seed parent with a proprietary selection of *Kalanchoe blossfeldiana* identified as code number 95-295-3, not patented, as the male pollen parent. Comparisons between the new variety and its parents cannot be made, as the parental varieties no longer exist. The cultivar 'Forever Midi Pink Morning' was discovered and selected in a controlled environment in Lompoc, Calif. Asexual reproduction of the new variety by terminal vegetative cuttings taken in Lompoc, Calif., has shown that the unique features of this new variety are stable and reproduced true to type in successive propagations.

The following traits have been repeatedly observed and are determined to be the unique characteristics of 'Forever Midi Pink Morning'. Characteristics that distinguish 'Forever Midi Pink Morning' as a new and distinct cultivar from others known to the breeder include:

1) Compact mounded habit;
2) Good lateral and basal branching;

3) No heat delay with night temperatures of 22° C.;
4) Distinct flower color opening as a light yellow, fading to near pinkish-white, and finally fading to pink. The plant may have flowers of all three colors at one time;
5) Dense flower cluster over the top of the plant;
6) Excellent postproduction longevity; and
7) Early to flower, flowering 8.5 to 9.5 weeks after start of short day treatment under summer conditions.

Plants of the new variety can be compared to plants of the *Kalanchoe* cultivar 'Forever Midi Sunset Pink', disclosed in U.S. Plant Pat. No. 12,371. In side-by-side comparisons conducted in Lompoc, Calif., plants of the new variety differed from plants of the cultivar 'Forever Midi Sunset Pink' in the following characteristics:

1) Flower color of the new variety was 7D to 27D to 56C, whereas the flower color of 'Forever Midi Sunset Pink' was 15A to 19B and 38C to 39C;
2) The new variety was shorter than 'Forever Midi Sunset Pink';
3) Time to flower in the summer from the start of short day treatment for the new variety was 8.5 to 9.5 weeks, whereas the time to flower for 'Forever Midi Sunset Pink' was 9 to 10 weeks; and
4) Leaf color of the new variety was 147A, whereas the leaf color of 'Forever Midi Sunset Pink' was 146B with a cast to the leaf edges of 181B.

BRIEF DESCRIPTION OF THE DRAWING

The accompanying colored photographic drawing illustrates the overall appearance of the new variety with the colors being as nearly true as is possible to obtain in colored illustrations of this type.

DESCRIPTION OF THE PLANT

Figure 1:
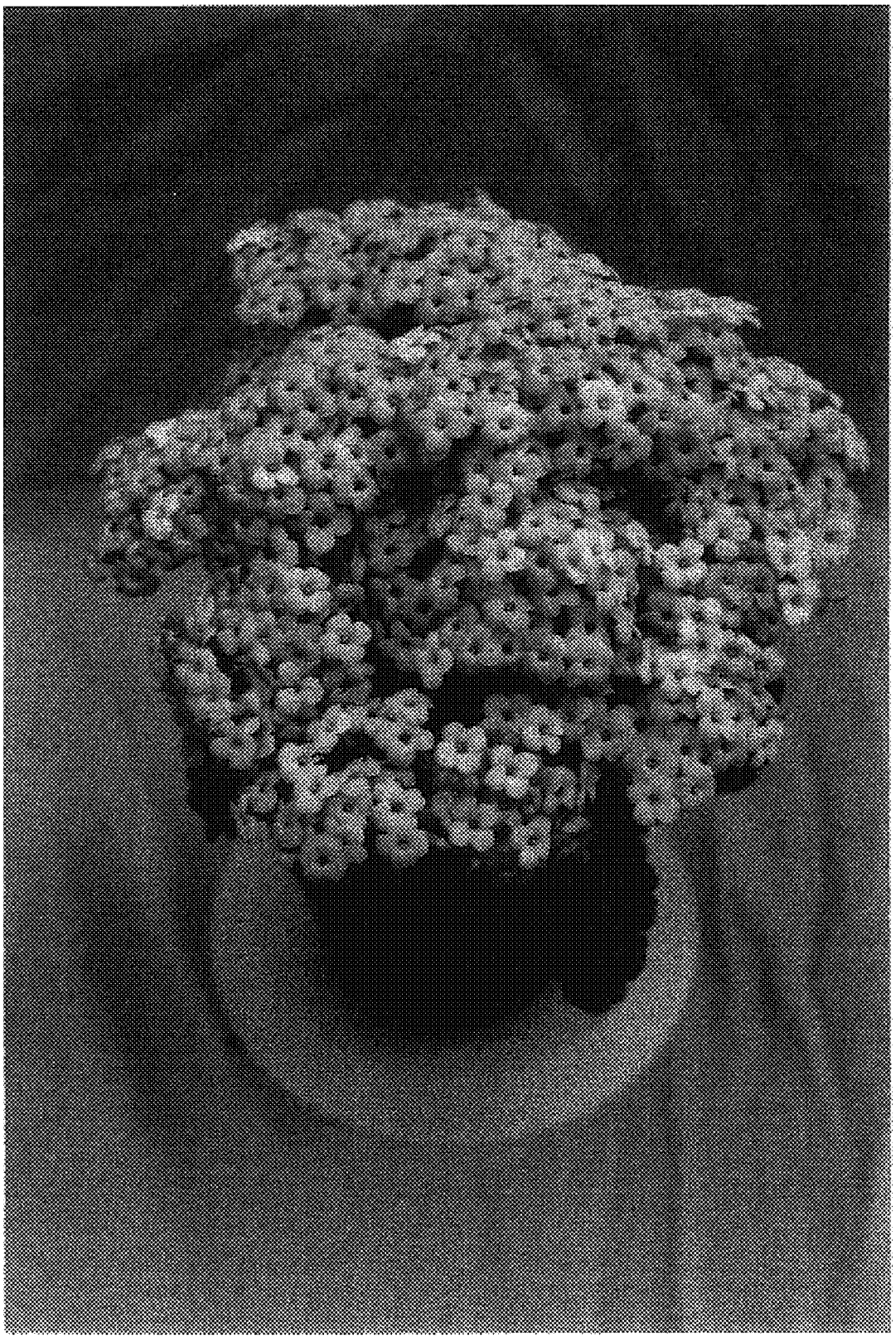

The cultivar 'Forever Midi Pink Morning' has not been observed under all possible environmental conditions. The phenotype may vary somewhat with variations in environment such as temperature, day length and light intensity. However, there is no variance in genotype.

In the following description, color references are made to The Royal Horticultural Society Colour Chart, 1995 Edition, except where general terms of ordinary dictionary significance are used. Plants were grown during the late winter through early spring of 2003 in Lompoc, Calif., in a corrugated polycarbonate-covered greenhouse with 30% shade covering. During the production of the plants, day temperatures ranged from 20 to 22° C.; night temperatures ranged from 16 to 18° C. and light levels averaged 4000 foot candles of light. Rooted cuttings were planted in 10 cm containers and received long day/short night conditions (more than 14 hours of light) for about three weeks; plants then received natural short day/long night conditions (minimum 14 hours darkness) until flowering. Plants were about 11 weeks from the start of the short day/long night treatment when the photograph and the description were taken.

Propagation:

*Type cutting.*—Terminal vegetative cuttings.

*Time to initiate roots.*—Summer: About 10 days at 21° C. Winter: About 12 days at 21° C.

*Time to produce a rooted cutting.*—Summer: About 21 days at 21° C. Winter: About 21 days at 21° C.

*Root description.*—Fine fibrous, freely branching, moderately dense, and grayed white in color.

Plant description:

*Form.*—Mounded to semi-upright, and dense plant habit. Freely flowering with numerous compound cymes. Inverted triangle; mounded crown. Appropriate for 10 cm containers; vigorous growth habit.

*Plant height at flowering.*—About 15 cm.

*Plant diameter at flowering.*—About 20 to 22 cm.

*Branching habit.*—Freely branching habit; typically 8 to 10 lateral branches develop per plant. Pinching (removal of terminal apex) is not required but will enhance lateral branch development.

*Lateral branch description.*—Length: About 9 to 11 cm. Diameter: About 3 to 4 mm. Internode length: About 6 to 8 mm. Aspect: About 35 to 40° from vertical. Strength: Strong. Texture: Smooth, glabrous. Color: 146C.

*Foliage description.*—Arrangement: Opposite, simple. Length: About 9 to 10 cm. Width: About 6 to 7 cm. Shape: Ovate. Apex: Acute to obtuse. Base: Acute to rounded. Margin: Crenate, moderate lobes, shallow cut. Texture, upper and lower surfaces: Coriaceous, glabrous, and succulent. Venation pattern: Pinnate. Color: Developing leaves, upper surface: 146A. Developing leaves, lower surface: 146B. Fully expanded leaves, upper surface: 147A. Fully expanded leaves, lower surface: 147B. Venation, upper surface: 147A. Venation, lower surface: 147B. Petiole length: About 8 to 10 mm. Petiole diameter: About 6 mm. Petiole texture: Smooth, glabrous. Petiole color, upper surface: 147A. Petiole color, lower surface: 146A.

Flower description:

*Flower type and habit.*—Single flowers arranged in axillary compound dichasial cymes. Freely flowering; more than 40 flowers per lateral branch and more than 250 flowers per plant. Flowers not persistent. Flowers not fragrant. Flowers face mostly upright.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about 8.5 to 9.5 weeks are required. Actual time to flower is primarily dependent upon temperature and light intensity.

*Post-production longevity.*—Excellent post-production longevity; plants maintain good foliage and flower substance for at least four weeks under interior environmental conditions. Individual flowers last for about 2 weeks.

*Flower diameter.*—About 1.5 cm.

*Flower height.*—About 1.2 cm.

*Flower buds.*—Shape: Oblong. Length: About 1.4 cm. Width: About 3 mm. Color: 146C, towards apex, 61B.

*Petals.*—Quantity: Four fused at base. Length: About 9 mm. Width: About 7 mm. Shape: Ovate to rounded. Apex: Cuspidate. Margin: Entire. Texture, upper and lower surfaces: Glabrous, smooth, soft. Color: When opening, upper surface: 7D. When opening, lower surface: 8D to 49B. Fully opened, upper surface: 27D, fading to 56C. Fully opened, lower surface: 27D to 50D, fading to 56D.

*Sepals.*—Quantity: Four fused at base. Length: About 7 mm. Width: About 2 mm. Shape: Lanceolate. Apex: Acuminate. Base: Rounded. Margin: Entire. Texture, upper and lower surfaces: Glabrous, smooth. Color: Immature, upper surface: 146D. Immature, lower surface: 146C. Mature, upper surface: 146C. Mature, lower surface: 146B.

*Calyx.*—Shape: Cupped. Length: About 8 mm. Diameter: About 3 mm.

*Peduncles.*—Length: About 2 cm. Diameter: About 2 mm. Angle: About 45° from vertical. Strength: Strong. Texture: Smooth, glabrous. Color: 146C.

*Pedicels.*—Length: About 3 mm. Diameter: About 1 mm. Angle: About 45°. Pedicel strength: Strong. Texture: Smooth, glabrous. Color: 146C.

*Reproductive organs.*—Stamens: Quantity per flower: Eight. Anther shape: Elliptic, flat. Anther size: Less than 1 mm. Anther color: Yellowish Green. Pollen amount: Abundant. Pollen color: Yellow. Pistils: Quantity per flower: Four. Style length: About 2 mm. Style color: Light Yellowish Green. Stigma shape: Flat. Stigma color: White. Ovary color: 146C.

*Seed.*—Quantity per ovary: More than 100. Length: Less than 1 mm. Diameter: Less than 1 mm.

Disease/pest resistance: Plants of the new variety have not been observed to date to be resistant to pathogens and pests common to *Kalanchoes*.

Temperature tolerance: Plants of the new variety have been observed to tolerate low temperatures of 10° C. and high temperatures of 35° C.

I claim:

1. A new and distinct variety of *Kalanchoe* plant named 'Forever Midi Pink Morning' as herein described and illustrated.

* * * * *